(12) United States Patent
Kumano et al.

(10) Patent No.: US 9,024,070 B2
(45) Date of Patent: May 5, 2015

(54) METHOD FOR PRODUCING XYLYLENEDIAMINE

(75) Inventors: Tatsuyuki Kumano, Kurashiki (JP); Yukiya Ibi, Kurashiki (JP); Kuniaki Arasuna, Kurashiki (JP); Shinichi Nagao, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 13/980,641

(22) PCT Filed: Jan. 30, 2012

(86) PCT No.: PCT/JP2012/051993
§ 371 (c)(1),
(2), (4) Date: Jul. 19, 2013

(87) PCT Pub. No.: WO2012/105498
PCT Pub. Date: Aug. 9, 2012

(65) Prior Publication Data
US 2013/0296609 A1  Nov. 7, 2013

(30) Foreign Application Priority Data

Jan. 31, 2011 (JP) ................................. 2011-019156

(51) Int. Cl.
*C07C 211/00* (2006.01)
*C07C 209/48* (2006.01)
(Continued)

(52) U.S. Cl.
CPC .............. *C07C 209/48* (2013.01); *B01J 23/002* (2013.01); *B01J 23/22* (2013.01); *B01J 23/26* (2013.01);
(Continued)

(58) Field of Classification Search
None
See application file for complete search history.

(56) References Cited

U.S. PATENT DOCUMENTS

| 3,803,204 A | 4/1974 | Grasselli et al. |
| 4,985,581 A | 1/1991 | Saito et al. |

(Continued)

FOREIGN PATENT DOCUMENTS

| CN | 1849291 A | 10/2006 |
| CN | 101128416 A | 2/2008 |

(Continued)

OTHER PUBLICATIONS

Combined Chinese Office Action and Search Report issued May 30, 2014 in Patent Application No. 201280007254.5 with English Translation of Category of Cited Documents.

(Continued)

*Primary Examiner* — Clinton Brooks
(74) *Attorney, Agent, or Firm* — Oblon, McClelland, Maier & Neustadt, L.L.P.

(57) ABSTRACT

Provided is a method for stably and economically producing xylylenediamine with a high yield and long catalyst service life by hydrogenating dicyanobenzene that is obtained by ammoxidating xylene. By bringing an aqueous basic solution into contact with a dicyanobenzene-absorbed liquid, which is obtained by bringing an ammoxidation reaction gas into contact with an organic solvent, under specified temperature conditions, and subjecting a base and a carboxylic acid in the dicyanobenzene-absorbed liquid to a neutralization reaction so as to form an aqueous phase that contains a water-soluble salt, and then subjecting an organic phase and the aqueous phase to liquid-liquid separation so as to remove the aqueous phase, it is possible to remove the carboxylic acid contained in the dicyanobenzene-absorbed liquid with high selectivity while inhibiting loss of the dicyanobenzene. By subjecting the raw material dicyanobenzene, which is obtained by separating low boiling point compounds from the post liquid-liquid separation organic phase by distillation under reduced pressure, to hydrogenation, xylylenediamine is produced with a high yield and the service life of the hydrogenation catalyst is extended.

11 Claims, 1 Drawing Sheet

(51) Int. Cl.

| | | |
|---|---|---|
| *B01J 23/22* | (2006.01) | |
| *B01J 23/26* | (2006.01) | |
| *B01J 37/00* | (2006.01) | |
| *B01J 23/00* | (2006.01) | |
| *B01J 23/75* | (2006.01) | |
| *B01J 23/755* | (2006.01) | |

(52) U.S. Cl.
 CPC .............. *B01J 23/75* (2013.01); *B01J 23/755* (2013.01); *B01J 37/0045* (2013.01); *B01J 2523/00* (2013.01)

(56) References Cited

U.S. PATENT DOCUMENTS

| | | | |
|---|---|---|---|
| 5,070,059 A | 12/1991 | Saito et al. | |
| 6,107,510 A | 8/2000 | Ebata et al. | |
| 7,323,598 B2 * | 1/2008 | Hugo et al. | 564/415 |
| 7,468,342 B2 * | 12/2008 | Kanamori et al. | 502/327 |
| 8,212,080 B2 * | 7/2012 | Kumano et al. | 564/375 |
| 2002/0038054 A1 | 3/2002 | Nakamura et al. | |
| 2002/0177735 A1 | 11/2002 | Kanamori et al. | |
| 2003/0013917 A1 | 1/2003 | Nakamura et al. | |
| 2004/0002614 A1 | 1/2004 | Amakawa et al. | |
| 2006/0258889 A1 | 11/2006 | Hugo et al. | |
| 2007/0010693 A1 | 1/2007 | Hugo et al. | |
| 2007/0027345 A1 | 2/2007 | Hugo et al. | |
| 2007/0088178 A1 | 4/2007 | Hugo et al. | |
| 2007/0088179 A1 | 4/2007 | Hugo et al. | |
| 2008/0091049 A1 | 4/2008 | Hugo et al. | |
| 2008/0154061 A1 * | 6/2008 | Ernst et al. | 564/372 |
| 2010/0168474 A1 | 7/2010 | Kumano et al. | |

FOREIGN PATENT DOCUMENTS

| | | |
|---|---|---|
| CN | 101768083 A | 7/2010 |
| EP | 1 262 232 A1 | 12/2002 |
| GB | 1 351 523 A | 5/1971 |
| JP | 38-008719 B1 | 6/1963 |
| JP | 49-013141 A | 2/1974 |
| JP | 49-45860 B1 | 12/1974 |
| JP | 53-020969 B2 | 6/1978 |
| JP | 63-190646 A | 8/1988 |
| JP | 01-275551 A | 11/1989 |
| JP | 05-170724 A | 7/1993 |
| JP | 09-071561 A | 3/1997 |
| JP | 11-246506 A | 9/1999 |
| JP | 2002-105035 A | 4/2002 |
| JP | 2003-026639 A | 1/2003 |
| JP | 2003-038956 A | 2/2003 |
| JP | 2003-267942 A | 9/2003 |
| JP | 2004-035427 A | 2/2004 |
| JP | 2007-505066 A | 3/2007 |
| JP | 2007-505067 A | 3/2007 |
| JP | 2007-505068 A | 3/2007 |
| JP | 2008-531521 A | 8/2008 |
| JP | 2010-168374 A | 8/2010 |

OTHER PUBLICATIONS

English translation of the International Search Report issued Apr. 24, 2012 in PCT/JP2012/051993.

* cited by examiner

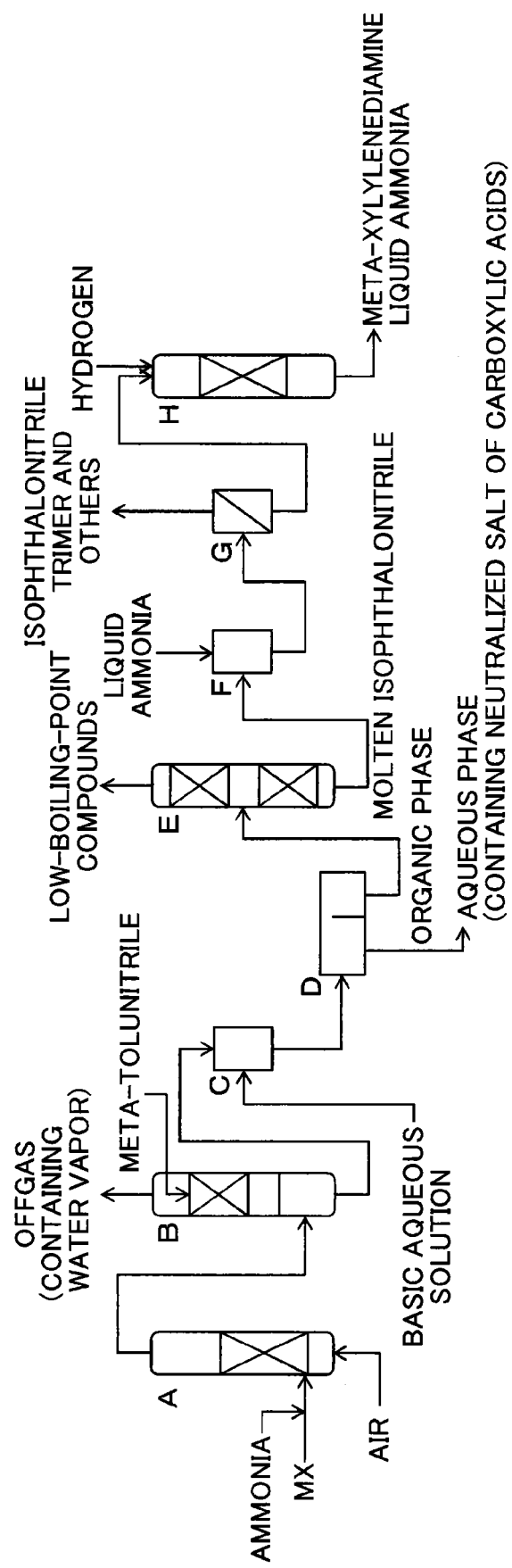

METHOD FOR PRODUCING XYLYLENEDIAMINE

TECHNICAL FIELD

The present invention relates to a method for producing xylylenediamine by hydrogenating dicyanobenzene obtained by ammoxidizing xylene. Xylylenediamine is a useful compound as raw materials of polyamide resins, hardeners, and the like, as well as intermediate raw materials of isocyanate resins and the like.

BACKGROUND ART

Dicyanobenzene can be produced by known methods of ammoxidizing xylene (ortho-xylene, meta-xylene, para-xylene), and can be produced, for example, by the methods described in Patent Literatures 1 to 8.

Various methods have been disclosed for production of xylylenediamine by subjecting dicyanobenzene to liquid-phase hydrogenation in the presence of a catalyst. For example, Patent Literature 9 states that a batch-wise hydrogenation reaction on dicyanobenzene is carried out in an alcohol-based solvent in an autoclave using a small amount of a caustic alkali agent together with Raney nickel or Raney cobalt to obtain corresponding xylylenediamine. Patent Literature 10 states that a catalytic reduction on dicyanobenzene with hydrogen is carried out in a liquid phase via a nickel-copper-molybdenum-based catalyst, illustrating a fixed-bed continuous hydrogenation.

Patent Literature 11 describes a method for producing meta-xylylenediamine, including: a first distillation step of separating impurities having a boiling point higher than isophthalonitrile from isophthalonitrile obtained by an ammoxidation reaction on meta-xylene; a second distillation step of separating an organic solvent and hydrogenating the isophthalonitrile obtained from a column bottom, by adding a specific solvent and liquid ammonia thereto. Patent Literature 12 describes a method for producing xylylenediamine, including: bringing a xylene-ammoxidation reaction gas into contact with an organic solvent or molten dicyanobenzene; separating a component having a boiling point lower than dicyanobenzene from the resulting organic solvent solution or suspension or dicyanobenzene melt; subsequently removing a component having a boiling point higher than dicyanobenzene; and then hydrogenating the dicyanobenzene.

Patent Literature 13 states that when dicyanobenzene is hydrogenated, benzamide compounds or benzoic acid compounds, which are impurities having a boiling point higher than dicyanobenzene, are separated by distillation to keep the concentration of the benzamides or benzoic acid compounds in the hydrogenation reaction solution at a specific level or lower, thereby producing xylylenediamine in a high yield and prolonging the catalyst service life. Patent Literature 14 describes a method for producing xylylenediamine, including: separating by distillation a component having a boiling point lower than dicyanobenzene from an organic solvent solution obtained by bringing a xylene-ammoxidation reaction gas into contact with an organic solvent; then, dissolving molten dicyanobenzene in a solvent containing liquid ammonia; and subjecting precipitates containing dicyanobenzene polymers to solid-liquid separation and hydrogenation.

Patent Literature 15 describes a method for producing xylylenediamine, including: bringing a xylene-ammoxidation reaction gas into contact with an organic solvent; and carrying out a hydrogenation reaction on dicyanobenzene absorbed in the organic solvent, without separation, by adding liquid ammonia. Patent Literature 16 describes a method for producing xylylenediamine, including: bringing a xylene-ammoxidation reaction gas into contact with an organic solvent or molten dicyanobenzene; separating a component having a boiling point lower than dicyanobenzene from the obtained organic solvent solution or suspension or dicyanobenzene melt; and then carrying out hydrogenation of the dicyanobenzene without removing a component having a boiling point higher than dicyanobenzene.

CITATION LIST

Patent Literatures

Patent Literature 1: Japanese Examined Patent Application Publication No. Sho 49-45860
Patent Literature 2: Japanese Patent Application Publication No. Sho 49-13141
Patent Literature 3: Japanese Patent Application Publication No. Sho 63-190646
Patent Literature 4: Japanese Patent Application Publication No. Hei 1-275551
Patent Literature 5: Japanese Patent Application Publication No. Hei 5-170724
Patent Literature 6: Japanese Patent Application Publication No. Hei 9-71561
Patent Literature 7: Japanese Patent Application Publication No. Hei 11-246506
Patent Literature 8: Japanese Patent Application Publication No. 2003-267942
Patent Literature 9: Japanese Examined Patent Application Publication No. Sho 38-8719
Patent Literature 10: Japanese Examined Patent Application Publication No. Sho 53-20969
Patent Literature 11: Japanese Patent Application Publication No. 2003-26639
Patent Literature 12: Published Japanese Translation of PCT Internal Application No. 2007-505068
Patent Literature 13: Japanese Patent Application Publication No. 2004-35427
Patent Literature 14: Japanese Patent Application Publication No. 2010-168374
Patent Literature 15: Japanese Patent Application Publication No. 2002-105035
Patent Literature 16: Published Japanese Translation of PCT Internal Application No. 2007-505067

SUMMARY OF INVENTION

Technical Problems

Xylylenediamine can be produced in a high yield by increasing the rate of progress of the hydrogenation reaction from nitrile groups to aminomethyl groups (for example, by increasing the conversion rate of nitrile groups and the selectivity into aminomethyl groups) in the hydrogenation of dicyanobenzene. Thus, in order to produce xylylenediamine by hydrogenating dicyanobenzene efficiently for a long time, it is necessary to keep the rate of progress of the hydrogenation reaction high as long as possible by suppressing the inactivation of the hydrogenation catalyst. Specifically, as the hydrogenation catalyst becomes more inactive, the concentrations of dicyanobenzene and cyanobenzylamine become higher in the resulting solution after the hydrogenation reaction. Accordingly, by keeping these concentrations low for a long period time to thereby hydrogenate a larger amount of dicyanobenzene, xylylenediamine can be obtained in a high yield for a long time.

The inactivation of the hydrogenation catalyst due to a compound having a boiling point higher than dicyanobenzene (hereinafter abbreviated as high-boiling-point compound) contained in dicyanobenzene can be avoided by separating the high-boiling-point compound by distillation as described in Patent Literatures 11 to 13. Nevertheless, separation of the high-boiling-point compound by distillation is not economically advantageous because the separation requires the cost for the distillation column construction and the energy for the distillation; besides, part of dicyanobenzene is degraded by polymerization with heat during the distillation. For example, Patent Literature 11 states in Example 1 that when the high-boiling-point compound was separated from isophthalonitrile by distillation with a column bottom temperature at 204° C., 2% of isophthalonitrile was degraded by heat. On the other hand, the method described in Patent Literature 14 in which a high-boiling-point compound is not separated by distillation is capable of removing a phthalonitrile polymer produced while a compound having a boiling point lower than dicyanobenzene (hereinafter abbreviated as low-boiling-point compound) is separated by distillation. However, this method has a problem of being incapable of removing other high-boiling-point compounds, for example, carboxylic acids typified by cyanobenzoic acid, which inactivate the hydrogenation catalyst.

For this reason, the development of a method for highly selectively removing high-boiling-point compounds inactivating the hydrogenation catalyst has been demanded in order to economically produce xylylenediamine.

An object of the present invention is to provide a method for producing xylylenediamine by hydrogenating dicyanobenzene obtained by ammoxidizing xylene, by which xylylenediamine is economically produced in a high yield stably with a long catalyst service life.

Solution to Problems

In the course of studies on xylylenediamine production by hydrogenating dicyanobenzene, the present inventors have found the following facts. Specifically, when an ammoxidation reaction gas is brought into contact with an organic solvent, a dicyanobenzene-absorbed liquid is obtained. When this dicyanobenzene-absorbed liquid is brought into contact with a basic aqueous solution, a base and carboxylic acids in the dicyanobenzene-absorbed liquid form a water-soluble salt by a neutralization reaction. After an aqueous phase containing this water-soluble salt is formed, if the aqueous phase is removed by subjecting the aqueous phase and an organic phase to liquid-liquid separation, this makes it possible to highly selectively remove carboxylic acids contained in the dicyanobenzene-absorbed liquid; in addition, performing this operation under a temperature condition of 140° C. or lower, it is possible to suppress productions of cyanobenzamide, cyanobenzoic acid, and phthalamides from the dicyanobenzene as well as the dissolution of the dicyanobenzene into the aqueous phase. Such effects in the present invention could have not been expected because it has been known from Japanese Patent Application Publication Nos. 2000-86610 and Sho 52-39648 and so forth that a large amount of cyanobenzamide is produced by a hydration reaction of dicyanobenzene under a basic condition. Furthermore, the present invention has found out that the operations from the contacting with the basic aqueous solution to the separation described above can be performed on dicyanobenzene in a solution form, and as a result, provides an industrially superior production method. For example, a method in which carboxylic acids contained in solid dicyanobenzene is removed by solid-liquid extraction using a basic aqueous solution brings about the purification effect only on the solid surface; further, capital investment costs are incurred for operations required after the solid-liquid extraction, for example, solid-liquid separation, drying, and so on. Additionally, a transfer pipe for transferring dicyanobenzene in a solid or slurry state is likely to be clogged. Hence, the method is not industrially suitable. Meanwhile, for example, in a method in which molten dicyanobenzene is brought into contact with a basic aqueous solution, the temperature during the contacting is high because the melting point of dicyanobenzene is high. For this reason, the method is industrially disadvantageous in terms of increased amounts of cyanobenzamide, cyanobenzoic acid, and phthalamides produced from dicyanobenzene and in terms of increased capital investment costs due to the high operating pressure.

The present invention has further discovered that by hydrogenating a raw material dicyanobenzene obtained by separating by distillation under reduced pressure a low-boiling-point compound from an organic phase after liquid-liquid separation, xylylenediamine is obtained in a high yield and the inactivation of a hydrogenation catalyst is suppressed.

Specifically, the present invention is a method for producing xylylenediamine, characterized in that the method includes the following steps:

(1) an absorption step of bringing a xylene-ammoxidation reaction gas containing dicyanobenzene into direct contact with an organic solvent, thereby absorbing the dicyanobenzene in the organic solvent;

(2) an extraction step of bringing the dicyanobenzene-absorbed liquid from the absorption step into contact with a basic aqueous solution under a temperature condition of 140° C. or lower, and extracting into an aqueous phase a water-soluble salt formed by a neutralization reaction between a base and carboxylic acids in the dicyanobenzene-absorbed liquid;

(3) a liquid-liquid separation step of separating a solution mixture of the dicyanobenzene-absorbed liquid and the basic aqueous solution from the extraction step into an organic phase and an aqueous phase;

(4) a low-boiling-point compound separation step of distilling the organic phase from the liquid-liquid separation step, thereby separating part or all of the components having a boiling point lower than the dicyanobenzene including the organic solvent to obtain molten dicyanobenzene; and (5) a hydrogenation step of dissolving the molten dicyanobenzene from the low-boiling-point compound separation step in a solvent, followed by liquid phase hydrogenation in the presence of a catalyst.

Advantageous Effects of Invention

The present invention makes it possible to produce xylylenediamine by hydrogenating dicyanobenzene obtained by ammoxidizing xylene such that xylylenediamine is economically produced in a high yield stably with a long catalyst service life.

BRIEF DESCRIPTION OF DRAWING

FIG. 1 is a process flow sheet for illustrating an embodiment of the present invention, that is, steps of producing isophthalonitrile by an ammoxidation reaction, and then producing meta-xylylenediamine by a hydrogenation reaction on the isophthalonitrile. In FIG. 1, A denotes an ammoxidation reactor, B denotes an isophthalonitrile absorption column, C denotes a mixing tank, D denotes a liquid-liquid separation tank, E denotes a distillation column, F denotes a dissolution tank, G denotes a filter, and H denotes a hydrogenation reactor.

DESCRIPTION OF EMBODIMENT

In the present invention, dicyanobenzene refers to three isomers of phthalonitrile (1,2-dicyanobenzene), isophthalonitrile (1,3-dicyanobenzene), and terephthalonitrile (1,4-dicyanobenzene). Each dicyanobenzene is produced from corresponding xylene, ortho-xylene, meta-xylene, or para-xylene by a known ammoxidation method. Hydrogenating dicyanobenzene produces corresponding xylylenediamine, that is, ortho-xylylenediamine, meta-xylylenediamine, and para-xylylenediamine. A method of the present invention is particularly preferably used for producing meta-xylylenediamine by hydrogenating isophthalonitrile obtained by ammoxidizing meta-xylene.

The production method of the present invention includes steps illustrated below.

(1) Absorption Step

A xylene-ammoxidation reaction gas containing dicyanobenzene is brought into direct contact with an organic solvent, thereby absorbing the dicyanobenzene in the organic solvent.

The ammoxidation reaction can be carried out by a known method. A reaction raw material mixture of xylene, oxygen, and ammonia is supplied to a catalyst for the ammoxidation reaction, and reacted with each other for the ammoxidation reaction under conditions describe later. The ammoxidation reaction may be carried out in either a fluidized bed manner or a fixed bed manner. As the catalyst for the ammoxidation, it is possible to use known catalysts, for example, a catalyst described in Patent Literature 1, 4, 5, 7, or 8. A catalyst containing vanadium and/or chromium is particularly preferable. The amount of ammonia used is in a range of preferably 2 to 20 moles, more preferably 6 to 15 moles, relative to 1 mole of xylene. If the amount used is within the aforementioned range, the yield of dicyanobenzene is favorable, and the space time yield is also high. Unreacted ammonia contained in the ammoxidation reaction gas may be recovered and reused for the reaction. The amount of oxygen used is in a range of preferably 3 moles or higher, more preferably 3 to 100 moles, and further preferably 4 to 100 moles, relative to 1 mole of xylene. If the amount is within the aforementioned range, the yield of dicyanobenzene is favorable, and the space time yield is also high. Air may be used as the supply source of oxygen. The reaction temperature of the ammoxidation is in a range of preferably 300 to 500° C., more preferably 330 to 470° C. If the temperature is within the aforementioned range, the conversion rate of xylene is favorable, productions of carbon dioxide, hydrogen cyanide, and the like are suppressed; hence, dicyanobenzene can be produced in a favorable yield. The reaction pressure of the ammoxidation may be ordinary pressure, increased pressure, or reduced pressure. The reaction pressure is preferably in a range of ordinary pressure (atmospheric pressure) to 300 kPa. The space velocity (Gas Hourly Space Velocity=GHSV) of the reaction raw material is preferably 500 to 5000 $h^{-1}$.

In this step, the phrase "absorbing the dicyanobenzene in the organic solvent" means that the dicyanobenzene in the ammoxidation reaction gas is dissolved in the organic solvent. The organic solvent used for absorbing the dicyanobenzene refers to one having a boiling point lower than the dicyanobenzene, having a relatively high solubility for the dicyanobenzene, and being inert to the dicyanobenzene. A preferable organic solvent meeting these requirements is at least one organic solvent selected from alkylbenzenes such as xylene (ortho-xylene, meta-xylene, para-xylene), pseudocumene, mesitylene, and ethylbenzene; heterocyclic compounds such as methylpyridine; aromatic nitrile compounds such as tolunitrile (ortho-tolunitrile, meta-tolunitrile, para-tolunitrile) and benzonitrile; and heterocyclic nitrile compounds such as cyanopyridine. Tolunitrile is particularly suitable in the present invention. In the absorption step, the ammoxidation reaction gas is preferably brought into contact with the organic solvent at 80 to 200° C. for 1 to 30 seconds. The amount of the organic solvent used is preferably 0.5 to 20 parts by weight relative to 1 part by weight of the dicyanobenzene. The organic solvent and the ammoxidation reaction gas can be brought into contact with each other using a gas-liquid contactor or the like, in either a counterncurrent manner or a cocurrent manner. Alternatively, the two may also be brought into contact with each other, for example, by providing a gas inlet at a bottom portion of a container containing the organic solvent for feeding the ammoxidation reaction gas into the solvent solution.

(2) Extraction Step

The dicyanobenzene-absorbed liquid from the absorption step is brought into contact with a basic aqueous solution, and a water-soluble salt formed by a neutralization reaction between a base and carboxylic acids in the dicyanobenzene-absorbed liquid is extracted into an aqueous phase. Herein, the carboxylic acids refer to cyanobenzoic acid (ortho-cyanobenzoic acid, meta-cyanobenzoic acid, para-cyanobenzoic acid), methylbenzoic acid (ortho-methylbenzoic acid, meta-methylbenzoic acid, para-methylbenzoic acid), or phthalic acid (ortho-phthalic acid, meta-phthalic acid, para-phthalic acid). In order to efficiently bring the dicyanobenzene-absorbed liquid into contact with the basic aqueous solution, a mixing tank having a stirrer may be used, or a tube type mixer such as a static mixer may be used. The extraction step may be performed in either a batch-wise manner, a semi-batch-wise manner, or a continuous manner. The base contained in the basic aqueous solution is not particularly limited, as long as a salt formed by the neutralization reaction between the base and the carboxylic acids in the dicyanobenzene-absorbed liquid is soluble in water. Preferable specific examples of the base include ammonia, sodium hydroxide, potassium hydroxide, sodium carbonate, potassium carbonate, and the like. Among these bases, ammonia is a particularly preferable base because ammonia is available at low cost and is capable of efficiently neutralizing the carboxylic acids in the dicyanobenzene-absorbed liquid. The amount of the base used (the number of moles) should be equal to or larger than a total number of moles of the carboxylic acids contained in the dicyanobenzene-absorbed liquid. For example, when ammonia is used, the number of moles of ammonia is preferably 1 to 50 times, further preferably 2 to 30 times, and particularly preferably 3 to 15 times the total number of moles of the carboxylic acids. The concentration of the base in the basic aqueous solution should be adjusted as appropriate, depending on the type of the base used. For example, when an ammonia aqueous solution is used, the concentration is preferably 0.1 to 20 wt %, and particularly preferably 0.1 to 10 wt %.

The amount of the basic aqueous solution used relative to the dicyanobenzene-absorbed liquid is not particularly limited, but is industrially desirably equivalent to or larger than that of the dicyanobenzene-absorbed liquid. For example, when an ammonia aqueous solution is used, the amount is preferably 1 to 100 wt %, further preferably 2 to 100 wt %, for example, 2 to 50 wt %, and particularly preferably 5 to 100 wt %, for example, 5 to 30 wt %, of the dicyanobenzene-absorbed liquid. As part or all of the basic aqueous solution, an aqueous phase recovered in the next step of a liquid-liquid separation step may be used. In consideration of the liquid-liquid separation operation in the next step, it is desirable that the basic aqueous solution contain at least one kind of ammonium salt in advance. If the ammonium salt is dissolved in the basic aqueous solution and is present therein together with the base, the liquid-liquid separation can be accelerated without adversely influencing the extraction of the carboxylic acids. The ammonium salt may be any of an ammonium salt of an inorganic acid and an ammonium salt of carbamic acid. The inorganic acid is preferably such an inorganic acid that the basicity of the aqueous solution can be maintained. The pH (25° C.) of the basic aqueous solution is, for example, 8 to 14, more preferably 9 to 13. The ammonium salt is preferably ammonium carbonate, ammonium hydrogen carbonate, ammonium carbamate, diammonium hydrogen carbonate carbamate, ammonium sulfate, and ammonium nitrate, each of which is used alone or in any combination. The amount of the ammonium salt used is adjusted as appropriate, depending on the separation speed required in the liquid-liquid separation step. The amount is normally adjusted in a way that the amount of the ammonium salt dissolved in the basic aqueous solution is 1 to 30 wt %. Among basic aqueous solutions containing the ammonium salt, particularly an aqueous solution in which ammonium carbonate and ammonia are dissolved is an industrially preferable basic aqueous solution because it can be prepared easily at low cost by passing a gas including carbon dioxide through ammonia water.

The temperature at which the dicyanobenzene-absorbed liquid and the basic aqueous solution are brought into contact with each other is preferably 140° C. or lower, further preferably 130° C. or lower, and particularly suitable 120° C. or lower, for example, 110° C. The temperature can be set in a range of, for example, 90° C. to 140° C., preferably 90° C. to 130° C., and more preferably 90° C. to 120° C. When the temperature is higher than 140° C., large amounts of cyanobenzamide, cyanobenzoic acid, and phthalamides are produced from the dicyanobenzene, and the solubility of the dicyanobenzene into the aqueous phase is also increased; hence, a large amount of dicyanobenzene is lost by this operation. No particular problem arises, as long as the lower limit of the contact temperature is within such a temperature range that the dissolved state of the dicyanobenzene in the dicyanobenzene-absorbed liquid can be maintained. For example, when a solution has an isophthalonitrile concentration of 25 wt % in which isophthalonitrile is absorbed in meta-tolunitrile, control has to be performed at a solution temperature of 90° C. or higher so as to prevent isophthalonitrile from precipitating. In order to bring the dicyanobenzene-absorbed liquid and the basic aqueous solution into contact with each other under low temperature condition (for example, 5 to 50° C., preferably 10 to 40° C., more preferably 20 to 30° C.), a fresh organic solvent may be added to the dicyanobenzene-absorbed liquid before the contact or during the contact. In order to reduce the amount of waste water, the aqueous phase recovered in the next step of the liquid-liquid separation step may be used as part or all of the basic aqueous solution described above. Meanwhile, an organic solvent may be added to this recovered aqueous phase to form an emulsion and to bring this emulsion into contact with the dicyanobenzene-absorbed liquid. A preferable organic solvent to be added is at least one organic solvent selected from alkylbenzenes such as xylene (ortho-xylene, meta-xylene, para-xylene), pseudocumene, mesitylene, and ethylbenzene; heterocyclic compounds such as methylpyridine; aromatic nitrile compounds such as tolunitrile (ortho-tolunitrile, meta-tolunitrile, para-tolunitrile) and benzonitrile; and heterocyclic nitrile compounds such as cyanopyridine. The organic solvent used in the absorption step is the most suitable. The pressure at the time of bringing the dicyanobenzene-absorbed liquid into contact with the basic aqueous solution is adjusted from atmospheric pressure to increased pressure condition as appropriate, depending on the temperature condition and the types of the base and ammonium salt used. Nevertheless, it is only necessary that the basic aqueous solution maintain the liquid phase, and that a required amount of the base be present in the aqueous phase. As necessary, an inert gas such as a nitrogen gas or an argon gas may also be present. The time during which the dicyanobenzene-absorbed liquid and the basic aqueous solution are brought into contact with each other varies, depending on the base used, but the time can be set for example within 2 hours, preferably within 1 hour, and more preferably within 30 minutes. Although depending on the method for bringing the dicyanobenzene-absorbed liquid into contact with the basic aqueous solution, the time from several seconds to 30 minutes is normally sufficient.

(3) Liquid-Liquid Separation Step

A solution mixture of the dicyanobenzene-absorbed liquid and the basic aqueous solution from the extraction step is separated into an organic phase and an aqueous phase. The separation can be conducted by a known method using a centrifuge, a coalescer, and a separator in combination, or other methods, besides a phase separation method in which the solution mixture is left standing. The temperature and pressure conditions of the liquid-liquid separation are desirably approximately the same as the conditions during the extraction. If the temperature and the pressure are greatly lowered, this causes not only the dicyanobenzene to precipitate in the organic phase, but also the dicyanobenzene dissolved in a small amount to precipitate in the aqueous phase, thereby causing pipe clogging and so forth.

(4) Low-Boiling-Point Compound Separation Step

The organic phase from the liquid-liquid separation step is distilled, thereby removing part or all of low-boiling-point compounds including the organic solvent to obtain molten dicyanobenzene. The distillation method is not particularly limited, as long as part or all of the low-boiling-point compounds including the organic solvent can be removed and molten dicyanobenzene can be obtained. It is possible to use either a batch-wise method or a continuous method. For example, when this step is performed using a distillation column, the low-boiling-point compounds including the organic solvent are removed from the column top or from both the column top and a side-cut portion (concentration section). The recovered solution may be used as the organic solvent for absorbing the dicyanobenzene contained in the ammoxidation reaction gas in the absorption step. The distillation using the distillation column is preferably conducted at a temperature at which the dicyanobenzene does not precipitate in the concentration section (located above a raw material feeding section) under reduced pressure (for example, the column top pressure is 1 to 30 kPa), and molten dicyanobenzene is obtained from the column bottom of the distillation column. The column bottom temperature is preferably set at a temperature equal to or higher than the melting point of dicyanobenzene but as low as possible so as to suppress the production of dicyanobenzene polymers due to heat. Specifically, the column bottom temperature is, when the dicyanobenzene is phthalonitrile, preferably 150 to 200° C., further preferably 150 to 180° C., and particularly preferably 150 to 170° C. In a case of isophthalonitrile, the temperature is preferably 170 to 220° C., further preferably 170 to 200° C., and particularly preferably 170 to 190° C. In a case of terephthalonitrile, the temperature is preferably 240 to 290° C., further preferably 240 to 270° C., and particularly preferably 240 to 260° C. Moreover, in order to suppress the production of dicyanobenzene polymers at the column bottom, the residence time of the molten dicyanobenzene is preferably as short as possible. For example, the residence time can be set within 180 minutes, for example, 5 to 180 minutes, preferably 10 to 120 minutes, more preferably 15 to 60 minutes, and particularly preferably 20 to 30 minutes. Further, in designing the distillation column, the volume of the column bottom is preferably as small as possible within such a range that the distillation column is operated without any trouble.

(5) Hydrogenation Step

The molten dicyanobenzene from the low-boiling-point compound separation step is dissolved in a solvent, and then the dicyanobenzene is subjected to liquid phase hydrogenation in the presence of a catalyst. Examples of the solvent include a liquid ammonia solvent, a solvent mixture of xylylenediamine and liquid ammonia, a solvent mixture of an aromatic hydrocarbon and liquid ammonia, a solvent mixture of xylylenediamine, an aromatic hydrocarbon, and liquid ammonia, and the like.

The higher the liquid ammonia concentration in the solvent, the higher the yield of the hydrogenation reaction. Accordingly, the liquid ammonia concentration in the solvent is preferably as high as possible (for example, 60 wt % or more (including 100 wt %)). The amount of the solvent during the hydrogenation reaction is preferably in a range of 1 to 99 parts by weight, further preferably 3 to 99 parts by weight, and particularly preferably in a range of 5 to 99 parts by weight, relative to 1 part by weight of the dicyanobenzene. If the amount of the solvent used is within the aforementioned range, less energy is required to recover the solvent, which is economically advantageous, making favorable the selectivity of xylylenediamine in the hydrogenation reaction, as well. The operation of dissolving the molten dicyanobenzene can be performed using a tube type mixer such as a static mixer. However, the adhesion of a precipitated insoluble component may clog the inside of the mixer. Hence, it is preferable to mix the molten dicyanobenzene with the solvent in a dissolution tank for the dissolution. Supplying the molten dicyanobenzene and the solvent into the dissolution tank enables the dissolution without particular stirring, but the dissolution may be performed under stirring if necessary. The pressure and the temperature in the dissolution tank are selected so as to maintain the solvent in a liquid phase. The pressure in the dissolution tank is preferably 0.5 to 15 MPa, further preferably 0.7 to 10 MPa, and particularly preferably 1 to 8 MPa. The solution temperature in the dissolution tank is preferably 3 to 140° C., further preferably 5 to 120° C., and particularly preferably 10 to 100° C. When an insoluble component is generated in the solution, part or all thereof may be removed by solid-liquid separation before supplied to a hydrogenation reactor. As the solid-liquid separation, it is possible to use a known method such as filtration, centrifugation, or sedimentation separation. Filtration is preferable, and filtration with a sintered metal filter and/or strainer is particularly convenient and suitable.

Hydrogen used for the hydrogenation may contain impurities not involved in the reaction, for example methane, nitrogen, or the like. Nevertheless, if the impurity concentration is high, the total pressure has to be increased so as to attain a necessary hydrogen partial pressure, which is industrially disadvantageous. Accordingly, the hydrogen concentration is preferably 50 mol % or more.

As the catalyst for the hydrogenation reaction, it is possible to use known supported metal catalysts, unsupported metal catalysts, Raney catalysts, noble metal catalysts, or the like. Particularly, a catalyst containing nickel and/or cobalt is suitably used. The amount of the catalyst used is not particularly limited in the present invention, as long as the amount is consistent with that used in known liquid phase hydrogenation of dicyanobenzene.

The hydrogenation reaction may be carried out in either a fixed bed manner or a suspension bed manner. In addition, the method may also be performed in either a batch-wise manner or a continuous manner. When a continuous flow reaction is carried out in a fixed bed reaction manner, a circulation method may be employed, in which a portion of a hydrogenation reaction solution obtained through an outlet of a hydrogenation reactor is continuously returned to the hydrogenation reactor. The circulation method may be employed alone, or the circulation method may be employed in combination with a one pass method as described in Japanese Patent Application Publication No. 2008-31155. When the reaction is carried out in a batch-wise manner, the hydrogenation reaction time is preferably 0.5 to 8 hours. When the reaction is carried out in a continuous manner, the space velocity (Liquid Hourly Space Velocity=LHSV) of the reaction raw material is preferably 0.1 to 10 $h^{-1}$.

The pressure and the temperature of the hydrogenation reaction are selected so as to maintain the solvent in a liquid phase. The temperature of the hydrogenation reaction is preferably 20 to 200° C., further preferably 30 to 150° C., and particularly preferably 40 to 120° C. The hydrogen pressure is preferably 1 to 30 MPa, further preferably 2 to 25 MPa, and particularly preferably 3 to 20 MPa.

In order to efficiently produce xylylenediamine by hydrogenating dicyanobenzene, it is essential to increase the rate of progress of the hydrogenation reaction from nitrile groups to aminomethyl groups. It is preferable to select reaction conditions so as to maintain the concentrations of dicyanobenzene and cyanobenzylamine low in the resulting solution after the hydrogenation reaction. Specifically, it is preferable to maintain the amount of cyanobenzylamine at 5.0 wt % or less relative to xylylenediamine in the resulting solution after the hydrogenation reaction. It is further preferable to maintain the amount at 1.0 wt % or less, and particularly preferable to maintain the amount at 0.2 wt % or less. Furthermore, the conversion rate of the dicyanobenzene is preferably 99.50% or more, further preferably 99.90% or more, and particularly preferably 99.95% or more. By appropriately selecting the temperature or the time in combination of the above-described reaction conditions (solvent, catalyst, raw material, hydrogen pressure, reaction manner, and so forth), the rate of progress of the hydrogenation reaction can be kept as described above.

The xylylenediamine produced by the hydrogenation can be purified by a known method such as distillation. If xylylenediamine having a higher purity is to be obtained, it is necessary to remove cyanobenzylamine contained in the xylylenediamine. However, the difference in boiling point between cyanobenzylamine and corresponding xylylenediamine is generally small, which makes it difficult to separate these compounds by normal distillation. Accordingly, a step of removing cyanobenzylamine by a method other than distillation may be provided before the distillation purification step. In this case, the method for removing cyanobenzylamine is not particularly limited. Examples thereof include a method in which cyanobenzylamine is converted by a hydration reaction to cyanobenzamide that can be relatively easily separated by distillation; a method in which a hydrogenation solvent of liquid ammonia is distilled off and then cyanobenzylamine is hydrogenated in the presence of a catalyst to reduce the amount of the cyanobenzylamine as described in Japanese Patent Application Publication No. 2007-332135; and the like.

EXAMPLES

Next, the present invention will be specifically described by way of the following Examples. It should be noted that the present invention is not limited to these Examples. Additionally, liquid chromatography was used to analyze impurities (including cyanobenzoic acid) contained in dicyanobenzene, and gas chromatography was used to analyze dicyanobenzene and analyze the composition of a solution produced by a hydrogenation reaction.

(1) Liquid Chromatography Analysis

The analysis was performed using a high-pressure gradient LC system with a UV-VIS detector manufactured by Shimadzu Corporation, which was equipped with CAPCELL PAK C18 LC column manufactured by Shiseido Company, Limited. A solution mixture of a 0.5-wt % aqueous solution of phosphoric acid and special grade acetonitrile manufactured by Wako Pure Chemical Industries, Ltd. was used as a solvent and mobile phase under conditions of: a column oven at 35° C., and a mobile-phase flow rate at 1.0 mL/minute.

(2) Gas Chromatography Analysis

The analysis was performed using a 6890 series GC analyzer manufactured by Agilent Technologies, Inc., which was equipped with DB-1 GC column manufactured by J&W Scientific Inc. The temperature was set as follows: the inlet was at 230° C.; the detector was at 295° C.; the column oven was increased from 100° C. to 280° C. (the temperature was held at 100° C. for 10 minutes, and then raised at a rate of 5° C./minute). Note that a GC measurement sample was prepared by removing ammonia (product manufactured by Mitsubishi Gas Chemical Company, Inc.) from a 2-ml sampling solution of a hydrogenation raw-material solution or a solution produced by the hydrogenation reaction by heating, and then adding to the resulting solution 0.1 g of diphenylmethane (manufactured by Wako Pure Chemical Industries, Ltd., special grade) as the internal standard, and dissolving the mixture in 10 g of a methanol solvent or a dioxane solvent (both manufactured by Wako Pure Chemical Industries, Ltd., special grade).

Example 1

(1) Absorption Step (1-1) Ammoxidation

To 229 g of vanadium pentoxide (manufactured by Wako Pure Chemical Industries, Ltd., special grade), 500 mL of water (distilled water) was added, and heated at 80 to 90° C. To this, 477 g of oxalic acid (manufactured by Wako Pure Chemical Industries, Ltd., special grade) was added and dissolved with stirring. Meanwhile, 400 mL of water was added to 963 g of oxalic acid and heated at 50 to 60° C., to which a solution obtained by adding 252 g of chromic anhydride (manufactured by Wako Pure Chemical Industries, Ltd., special grade) into 200 mL of water was added and dissolved with thorough stirring. The vanadium oxalate solution thus obtained was mixed with the chromium oxalate solution at 50 to 60° C. to obtain a vanadium-chromium solution. To this solution, 41.1 g of phosphomolybdic acid (manufactured by Nippon Inorganic Colour & Chemical Co., Ltd.) $H_3(PMo_{12}O_{40}) \cdot 20H_2O$ dissolved in 100 mL of water was added, and further 4.0 g of potassium acetate (manufactured by Wako Pure Chemical Industries, Ltd., special grade) dissolved in 100 mL of water was added. Then, 2500 g of a 20-wt % aqueous silica sol (containing 0.02 wt % of $Na_2O$) was added thereto. To this slurry solution, 78 g of boric acid was added and mixed well, followed by condensation by heating until the liquid amount became approximately 3800 g. This catalyst solution was spray-dried with the inlet temperature and the outlet temperature being kept at 250° C. and 130° C., respectively. After drying with a drier at 130° C. for 12 hours, the resultant was calcined at 400° C. for 0.5 hours, and calcined at 550° C. for 8 hours in air flow. This catalyst contained V:Cr:B:Mo:P:Na:K at an atomic ratio of 1:1:0.5:0.086:0.007:0.009:0.020, and the catalyst concentration was 50 wt %.

Subsequently, each step was carried out in accordance with the flow shown in FIG. 1. An ammoxidation reactor A was filled with 6 L of the above-prepared fluid catalyst. After air, meta-xylene (hereinafter abbreviated as MX, product manufactured by Mitsubishi Gas Chemical Company, Inc.), and ammonia (product manufactured by Mitsubishi Gas Chemical Company, Inc.) were mixed together, the mixture was preheated at a temperature of 350° C. and supplied to the reactor. The charging conditions were as follows: the amount of MX supplied was 350 g/h; the ammonia/MX molar ratio was 10; the oxygen/MX molar ratio was 5.4; and the space velocity GHSV was 630 $h^{-1}$. The reaction temperature was set at 420° C., and the reaction pressure was set at 0.2 MPa.

(1-2) Absorption

A reaction product gas from a top portion of the ammoxidation reactor A was introduced into an isophthalonitrile absorption column B. Isophthalonitrile in the reaction product gas was absorbed in a solvent of meta-tolunitrile (product manufactured by Mitsubishi Gas Chemical Company, Inc.). The isophthalonitrile absorption column B made of SUS304 has an upper portion provided with a discharging pipe, and a barrel portion with an inner diameter of 100 mmΦ and a height of 800 mm. The barrel portion has a lower portion 450 mm with a double tube structure so as to allow steam heating. The isophthalonitrile absorption column B has a bottom portion provided with a gas inlet. The absorption column was charged with 2 kg of meta-tolunitrile, and the temperature was set at 140° C. for absorption of the ammoxidation reaction product gas for 2 hours. When the absorption was completed, the isophthalonitrile-absorbed liquid contained 74.0 wt % of meta-tolunitrile, 25.0 wt % of isophthalonitrile, 0.131 wt % of 3-cyanobenzoic acid, 0.504 wt % of 3-cyanobenzamide, and 0.021 wt % of isophthalamide.

(2) Extraction Step

Next, a mixing tank C was charged with 100 g of the isophthalonitrile-absorbed liquid and hermetically sealed. Then, the temperature was adjusted with stirring at a speed of 1000 rpm in such a manner that the solution temperature was set at 110° C. The mixing tank C used was an autoclave (volume: 250 mL, having an extraction nozzle at a bottom portion thereof, made of SUS304) equipped with a heater and a stirrer. After the temperature of the isophthalonitrile-absorbed liquid was raised to a predetermined temperature, the pressure was increased to 0.1 MPaG with nitrogen. Subsequently, 0.80 g of 25% ammonia water (manufactured by Wako Pure Chemical Industries, Ltd., special grade) and 2.00 g of ammonium carbonate (manufactured by Wako Pure Chemical Industries, Ltd., special grade) were dissolved in 17.20 g of pure water to prepare a basic aqueous solution. After 20.0 g of the basic aqueous solution was supplied through the nozzle at the bottom portion of the mixing tank C, the solution temperature was adjusted again to 110° C. and held for 10 minutes while the stirring condition was kept at 1000 rpm.

(3) Liquid-Liquid Separation Step

The stirring in the mixing tank C was stopped, and a solution mixture of the isophthalonitrile-absorbed liquid and the basic aqueous solution was left standing for 10 minutes while the solution temperature condition was kept at 110° C. Thus, the solution mixture was separated into an organic phase (upper layer) and an aqueous phase (lower layer) (the mixing tank C was also used as a liquid-liquid separation tank D). After the liquid-liquid separation, 100 g of the organic phase contained 74.0 wt % of meta-tolunitrile, 24.9 wt % of isophthalonitrile, 0.020 wt % of 3-cyanobenzoic acid, 0.545 wt % of 3-cyanobenzamide, and 0.022 wt % of isophthalamide; meanwhile, 20.0 g of the aqueous phase contained 0.166 wt % of meta-tolunitrile, 0.154 wt % of isophthalonitrile, 0.732 wt % of 3-cyanobenzoic acid, 0.207 wt % of 3-cyanobenzamide, and 0.051 wt % of isophthalamide. Table 1 shows the composition of the organic phase and the percentage loss of isophthalonitrile from the extraction step to the liquid-liquid separation step.

(4) Low-Boiling-Point Compound Separation Step

The organic phase after the liquid-liquid separation was supplied to a middle portion of a distillation column E for separating low-boiling-point compounds in a continuous manner. The distillation conditions in the distillation column were as follows: the column top pressure was 5 kPa; the column top temperature was 120° C.; the column bottom temperature was 175° C.; and the residence time at the column bottom was 20 minutes. Meta-tolunitrile and other low-boiling-point compounds were distilled off from the column top of the distillation column, while the molten isophthalonitrile was drawn from the column bottom. The molten isophthalonitrile obtained from the column bottom contained 0.20 wt % of meta-tolunitrile, 96.9 wt % of isophthalonitrile, 0.08 wt % of 3-cyanobenzoic acid, and 2.59 wt % of 3-cyanobenzamide.

(5) Hydrogenation Step

In a dissolution tank F (made of SUS304), 1 part by weight of the molten isophthalonitrile thus obtained was dissolved in 9 parts by weight of liquid ammonia under conditions of 2 MPa and 25° C. Then, a solution containing an insoluble component was drawn from a bottom portion of the dissolution tank F, and filtered using a sintered metal filter (pore size: 40 μm, made of stainless steel) serving as a filter G by transferring the solution utilizing pressure difference. Thus, a hydrogenation raw-material solution was obtained.

A vertical tubular hydrogenation reactor H (made of SUS304, inner diameter: 13 mmϕ, volume: 50 mL) was filled with 15.0 g of a commercially-available supported nickel/diatomaceous earth catalyst (columnar shape, diameter: 3 mmΦ, height: 3 mm) with a nickel content of 50 wt %, the catalyst having been pulverized to have a uniform size (12 to 22 mesh/JIS standard). The catalyst was reduced under hydrogen stream at 200° C. and activated. After cooling, a hydrogen gas was introduced into the reactor by pressure to keep the pressure constant at 8 MPa. The temperature of the catalyst layer was maintained at 80° C. by heating from the outside. While a hydrogen gas was caused to flow through an upper portion of the reactor at a flow rate of 18 NL/h, the hydrogenation raw-material solution was continuously supplied at a speed of 33.0 g/h through the upper portion of the reactor. The amount of a reaction intermediate 3-cyanobenzylamine produced was increased over time. Table 2 shows the reaction results and a total amount of the isophthalonitrile solution fed to the reactor at the time when the amount of 3-cyanobenzylamine contained in the hydrogenation reaction solution reached 2.3 wt % of meta-xylylenediamine.

The liquid ammonia was separated from the hydrogenation reaction solution by simple distillation. Furthermore, the remaining ammonia was removed by bubbling of a nitrogen gas therethrough. Then, the reaction solution after the ammonia removal was again hydrogenated in a fixed bed reaction manner (WHSV (weight hourly space velocity)=0.5 h$^{-1}$, reaction temperature: 80° C., reaction pressure: 2 MPa) using a commercially-available supported nickel/diatomaceous earth catalyst with a nickel content of 50 wt %. Thus, crude meta-xylylenediamine was obtained. Then, the crude meta-xylylenediamine was distilled under a reduced pressure of 6 kPa using a distillation column with 10 theoretical plates to obtain purified meta-xylylenediamine with a purity of 99.99%. Note that the content of 3-cyanobenzylamine in the obtained meta-xylylenediamine was 0.001 wt % or less.

Example 2

The procedure of Example 1 was repeated up to the liquid-liquid separation step under the same conditions except that the solution temperature in the extraction step was set at 130° C. After the liquid-liquid separation, 100 g of the organic phase contained 73.9 wt % of meta-tolunitrile, 24.7 wt % of isophthalonitrile, 0.018 wt % of 3-cyanobenzoic acid, 0.639 wt % of 3-cyanobenzamide, and 0.024 wt % of isophthalamide; meanwhile, 20.0 g of the aqueous phase contained 0.401 wt % of meta-tolunitrile, 0.478 wt % of isophthalonitrile, 0.750 wt % of 3-cyanobenzoic acid, 0.386 wt % of 3-cyanobenzamide, and 0.151 wt % of isophthalamide. Table 1 shows the composition of the organic phase and the percentage loss of isophthalonitrile from the extraction step to the liquid-liquid separation step.

Example 3

The procedure of Example 1 was repeated up to the liquid-liquid separation step under the same conditions except that the solution temperature in the extraction step was set at 140° C. After the liquid-liquid separation, 100 g of the organic phase contained 73.8 wt % of meta-tolunitrile, 24.4 wt % of isophthalonitrile, 0.016 wt % of 3-cyanobenzoic acid, 0.736 wt % of 3-cyanobenzamide, and 0.030 wt % of isophthalamide; meanwhile, 20.0 g of the aqueous phase contained 0.944 wt % of meta-tolunitrile, 1.20 wt % of isophthalonitrile, 0.874 wt % of 3-cyanobenzoic acid, 0.476 wt % of 3-cyanobenzamide, and 0.156 wt % of isophthalamide. Table 1 shows the composition of the organic phase and the percentage loss of isophthalonitrile from the extraction step to the liquid-liquid separation step.

Example 4

The procedure of Example 1 was repeated up to the liquid-liquid separation step under the same conditions except that 20.0 g of the basic aqueous solution used in the extraction step was prepared by dissolving 0.10 g of sodium hydroxide (manufactured by Wako Pure Chemical Industries, Ltd., special grade) and 2.00 g of ammonium carbonate (manufactured by Wako Pure Chemical Industries, Ltd., special grade) in 17.90 g of pure water. After the liquid-liquid separation, 100 g of the organic phase contained 73.9 wt % of meta-tolunitrile, 24.9 wt % of isophthalonitrile, 0.007 wt % of 3-cyanobenzoic acid, 0.475 wt % of 3-cyanobenzamide, and 0.029 wt % of isophthalamide; meanwhile, 20.0 g of the aqueous phase contained 0.167 wt % of meta-tolunitrile, 0.154 wt % of isophthalonitrile, 0.877 wt % of 3-cyanobenzoic acid, 0.213 wt % of 3-cyanobenzamide, and 0.096 wt % of isophthalamide. The percentage loss of isophthalonitrile from the extraction step to the liquid-liquid separation step was 0.51 wt %.

Example 5

The procedure of Example 1 was repeated up to the liquid-liquid separation step under the same conditions except for the followings. In the extraction step, 12.8 g of the isophthalonitrile-absorbed liquid obtained in the absorption step was diluted with 87.2 g of meta-tolunitrile (manufactured by Wako Pure Chemical Industries, Ltd., special grade) to 100 g; 20.0 g of the basic aqueous solution used was prepared by dissolving 1.00 g of sodium hydroxide (manufactured by Wako Pure Chemical Industries, Ltd., special grade) in 19.00 g of pure water; and the step was performed under conditions of a solution temperature at 20° C. and atmospheric pressure. After the liquid-liquid separation, 100 g of the organic phase contained 96.6 wt % of meta-tolunitrile, 3.15 wt % of isophthalonitrile, 0.063 wt % of 3-cyanobenzamide, and 0.002 wt % of isophthalamide; meanwhile, 20.0 g of the aqueous phase contained 0.310 wt % of meta-tolunitrile, 0.004 wt % of isophthalonitrile, 0.079 wt % of 3-cyanobenzoic acid, 0.016 wt % of 3-cyanobenzamide, and 0.019 wt % of isophthalamide. The percentage loss of isophthalonitrile from the extraction step to the liquid-liquid separation step was 1.62 wt %.

Comparative Example 1

The procedure of Example 1 was repeated up to the hydrogenation step except that the isophthalonitrile-absorbed liquid obtained in the absorption step was supplied in the low-boiling-point compound separation step. Here, the molten isophthalonitrile obtained from the column bottom of the distillation column in the low-boiling-point compound separation step contained 0.20 wt % of meta-tolunitrile, 96.6 wt % of isophthalonitrile, 0.53 wt % of 3-cyanobenzoic acid, and 2.48 wt % of 3-cyanobenzamide.

Table 2 shows the reaction results and a total amount of the isophthalonitrile solution fed to the reactor at the time when the amount of 3-cyanobenzylamine contained in the hydrogenation reaction solution reached 2.3 wt % of meta-xylylenediamine as in Example 1.

Comparative Example 2

The procedure of Example 1 was repeated up to the liquid-liquid separation step under the same conditions except that the solution temperature in the extraction step was set at 150° C. After the liquid-liquid separation, 100 g of the organic phase contained 73.6 wt % of meta-tolunitrile, 24.1 wt % of isophthalonitrile, 0.015 wt % of 3-cyanobenzoic acid, 0.938 wt % of 3-cyanobenzamide, and 0.030 wt % of isophthalamide; meanwhile, 20.0 g of the aqueous phase contained 1.79 wt % of meta-tolunitrile, 1.84 wt % of isophthalonitrile, 0.955 wt % of 3-cyanobenzoic acid, 0.700 wt % of 3-cyanobenzamide, and 0.183 wt % of isophthalamide. Table 1 shows the composition of the organic phase and the percentage loss of isophthalonitrile from the extraction step to the liquid-liquid separation step.

TABLE 1

| | Isophthalonitrile-absorbed liquid | Example 1 | Example 2 | Example 3 | Comparative Example 2 |
|---|---|---|---|---|---|
| Solution temperature at extraction step (° C.) | | 110 | 130 | 140 | 150 |
| Composition of organic phase (wt %) | | | | | |
| meta-tolunitrile | 74.0 | 74.0 | 73.9 | 73.8 | 73.6 |
| isophthalonitrile | 25.0 | 24.9 | 24.7 | 24.4 | 24.1 |
| 3-cyanobenzoic acid | 0.131 | 0.020 | 0.018 | 0.016 | 0.015 |
| 3-cyanobenzamide | 0.504 | 0.545 | 0.639 | 0.736 | 0.938 |
| isophthalamide | 0.021 | 0.022 | 0.024 | 0.030 | 0.030 |
| Percentage loss of isophthalonitrile (wt %)*1 | 0.00 | 0.51 | 1.40 | 2.49 | 3.75 |

*1 percentage loss of isophthalonitrile [wt %] = (isophthalonitrile in isophthalonitrile-absorbed liquid [g] − isophthalonitrile in organic phase [g]) ÷ isophthalonitrile in isophthalonitrile-absorbed liquid [g] × 100

TABLE 2

| Reaction results (mol %) | Example 1 | Comparative Example 1 |
|---|---|---|
| Conversion rate of isophthalonitrile | >99.9 | >99.9 |
| Selectivity of meta-xylylenediamine | 84.3 | 82.5 |
| Selectivity of 3-cyanobenzylamine | 2.0 | 2.0 |
| Total amount of isophthalonitrile solution fed (g) | 255 | 182 |

INDUSTRIAL APPLICABILITY

The present invention makes it possible to produce xylylenediamine by hydrogenating dicyanobenzene obtained by ammoxidizing xylene such that xylylenediamine is economically produced in a high yield stably with a long catalyst service life.

REFERENCE SIGNS LIST

A ammoxidation reactor
B isophthalonitrile absorption column
C mixing tank
D liquid-liquid separation tank
E distillation column
F dissolution tank
G filter
H hydrogenation reactor

The invention claimed is:

1. A method for producing xylylenediamine, comprising:
   (i) bringing a xylene-ammoxidation reaction gas comprising a dicyanobenzene, which is obtained by ammoxidizing an xylene via an ammoxidation reaction, into direct contact with an organic solvent, thereby obtaining a dicyanobenzene-absorbed liquid comprising carboxylic acids;
   (ii) bringing the dicyanobenzene-absorbed liquid into contact with a basic aqueous solution comprising a base under a temperature of 140° C. or lower, and extracting into an aqueous phase a water-soluble salt formed by a neutralization reaction between the base and the carboxylic acids in the dicyanobenzene-absorbed liquid, thereby obtaining a solution mixture of the dicyanobenzene-absorbed liquid and the basic aqueous solution;
   (iii) separating the solution mixture of the dicyanobenzene-absorbed liquid and the basic aqueous solution into an organic phase and an aqueous phase;
   (iv) distilling the organic phase, thereby separating part or all of components having a boiling point lower than a boiling point of the dicyanobenzene-absorbed liquid to obtain a molten dicyanobenzene; and
   (v) dissolving the molten dicyanobenzene in a solvent, followed by a liquid phase hydrogenation in the presence of a hydrogenation catalyst, thereby obtaining the xylylenediamine.

2. The method according to claim 1, wherein
   the xylene is meta-xylene, and
   the dicyanobenzene is isophthalonitrile.

3. The method according to claim 1, wherein the base in (ii) is ammonia.

4. The method according to claim 1, wherein, in (ii), the basic aqueous solution comprises an ammonium salt of an inorganic acid, an ammonium salt of carbamic acid, or both.

5. The method according to claim 1, wherein the base in (ii) is ammonia with a number of moles of from 1 to 50 times a total number of moles of the carboxylic acids in the dicyanobenzene-absorbed liquid.

6. The method according to claim 1, wherein the ammoxidation reaction occurs in the presence of a catalyst comprising vanadium, chromium, or both.

7. The method according to claim 1, wherein the organic solvent in (i) is at least one selected from the group consisting of an alkylbenzene, a heterocyclic compound, an aromatic nitrile compound, and a heterocyclic nitrile compound.

8. The method according to claim 1, wherein the solvent in (v) is a liquid ammonia solvent, a solvent mixture of xylylenediamine and liquid ammonia, a solvent mixture of an aromatic hydrocarbon and liquid ammonia, or a solvent mixture of xylylenediamine, an aromatic hydrocarbon, and liquid ammonia.

9. The method according to claim 1, wherein the liquid phase hydrogenation in (v) is carried out in a fixed bed reactor.

10. The method according to claim 1, wherein the hydrogenation catalyst in (v) comprises nickel, cobalt, or both.

11. The method according to claim 1, wherein the hydrogenation catalyst in (v) comprises nickel.

* * * * *